(12) United States Patent
Ruan

(10) Patent No.: US 9,028,799 B2
(45) Date of Patent: May 12, 2015

(54) NITROIMIDAZOLE-AMINO ACID HYPOXIA CONTRAST MEDIUM, PREPARATION METHOD AND USE THEREOF

(76) Inventor: Jianping Ruan, Shenzhen (CN)

( * ) Notice: Subject to any disclaimer, the term of this patent is extended or adjusted under 35 U.S.C. 154(b) by 93 days.

(21) Appl. No.: 13/097,109

(22) Filed: Apr. 29, 2011

(65) Prior Publication Data

US 2011/0206604 A1    Aug. 25, 2011

Related U.S. Application Data

(63) Continuation of application No. PCT/CN2009/000246, filed on Mar. 9, 2009.

(30) Foreign Application Priority Data

Oct. 29, 2008  (CN) .......................... 2008 1 0201897

(51) Int. Cl.
| | | |
|---|---|---|
| A61K 51/00 | (2006.01) | |
| A61M 36/14 | (2006.01) | |
| A61K 51/04 | (2006.01) | |
| C07D 233/92 | (2006.01) | |
| C07D 233/95 | (2006.01) | |
| C07F 13/00 | (2006.01) | |

(52) U.S. Cl.
CPC .......... *A61K 51/0497* (2013.01); *A61K 51/0453* (2013.01); *C07D 233/92* (2013.01); *C07D 233/95* (2013.01); *C07F 13/005* (2013.01)

(58) Field of Classification Search
None
See application file for complete search history.

(56) References Cited

U.S. PATENT DOCUMENTS

| | | | | |
|---|---|---|---|---|
| 4,193,979 | A * | 3/1980 | Frank et al. .................. | 424/1.65 |
| 5,504,055 | A * | 4/1996 | Hsu ............................... | 504/121 |
| 7,261,875 | B2 * | 8/2007 | Li et al. ......................... | 424/1.69 |
| 2005/0079133 | A1 | 4/2005 | Yang et al. | |
| 2006/0246005 | A1 * | 11/2006 | Yang et al. .................... | 424/1.69 |

FOREIGN PATENT DOCUMENTS

| | | |
|---|---|---|
| CN | 1438899 A | 8/2003 |
| CN | 101203249 A | 6/2008 |
| EP | 1698351 A2 | 9/2006 |

OTHER PUBLICATIONS

Chakravarty et al. J. Inorg. Biochem. 39, 43-57 (1990).*
Rattat et al. Tetrahedron Lett. 45 (2004) 2531-2534.*
Dilworth et al. Curr. Direc. Radiopharm. Res. Develop. 1996; 1-29.*
Kong et al. J. Label Compd Radiopharm. 2007, 50, 1137-1142.*

* cited by examiner

*Primary Examiner* — Maria Leavitt
*Assistant Examiner* — Sean R Donohue
(74) *Attorney, Agent, or Firm* — Manni Li; Mei & Mark LLP

(57) ABSTRACT

A hypoxia contrast medium including nitroimidazole-amino acid chelate with a positively charged radioactive nuclide, a preparation method and use thereof. The contrast medium can be used in imaging cerebral thrombosis, tumors or other diseases such as ulceration, thrombosis, and so on.

1 Claim, 13 Drawing Sheets

NITROIMIDAZOLE-AMINO ACID HYPOXIA CONTRAST MEDIUM, PREPARATION METHOD AND USE THEREOF

CROSS-REFERENCE TO RELATED APPLICATIONS

This application is a continuation of International Patent Application No. PCT/CN2009/000246 with an international filing date of Mar. 9, 2009, designating the United States, and further claims priority benefits to Chinese Patent Application No. 200810201897.9 filed Oct. 29, 2008. The contents of all of the aforementioned applications, including any intervening amendments thereto, are incorporated herein by reference.

BACKGROUND OF THE INVENTION

1. Field of the Invention

The invention relates to a medical nuclear contrast medium, and more particularly to a nitroimidazole-amino acid hypoxia contrast medium, a precursor, preparation method, and use thereof.

2. Description of the Related Art

Tumors have become one of the major killers of human health. Malignant tumors usually need to be surgically removed, or be removed using chemotherapy or radiation. These therapies, however, have very negative effect on patients, since not only tumor cells will be killed, but also normal cells will be damaged to various degrees, which leads to mental affliction as well as decline in physical strength of the patients. Therefore, an early detection and diagnosis of tumors are very much desired, so that tumor cells can be eradicated at an early stage and the patients can obtain a new life. Scientists have already discovered that malignant tumors contain hypoxic cells and it is possible to detect tumor cells by testing cellular oxygen level. It has been reported that oxygen electrodes can be used to test cellular oxygen level. However, this method is very limited in terms of in vivo application. In recent years, nuclear technology has been applied in medical field for the detection of hypoxic tumor cells. Nuclear technology deploys hypoxia imaging technique which enables it to be detained in hypoxic cells, and then detects the oxygen level through imaging technology, which leads to the detection and diagnosis of malignant tumors. Nitroimidazole and their derivatives are used as radiation sensitizers. Their metabolisms inside cells are determined by the available cellular oxygen. Therefore, hypoxic cells can be imaged by labeling these compounds with radioactive nuclides. Nowadays, nuclear technology has become a focus of radiology medicine and hypoxia cellular imaging has also received a lot of attention. For example, $^{18}$FMISO, $^{99m}$Tc-HL91 and other compounds have been frequently used in clinic imaging research as hypoxia contrast medium. However, they possess a lot of drawbacks such as low absolute intake value by tumor cells, long imaging time and high cost, etc. As a result, a more effective tumor contrast medium is still in need.

SUMMARY OF THE INVENTION

In view of the above-described problems, it is one objective of the invention to provide a nitroimidazole or a derivative thereof as a contrast medium targeting hypoxia cells.

It is another objective of the invention to provide a precursor of the contrast medium.

It is still another objective of the invention to provide a method for preparation of the precursor.

To achieve the above objectives, in accordance with one embodiment of the invention, there is provided a hypoxia contrast medium comprising nitroimidazole-amino acid chelate with a positively charged radioactive nuclide.

In accordance with another embodiment of the invention, there is provided a precursor of the nitroimidazole-amino acid compound (Formula 1),

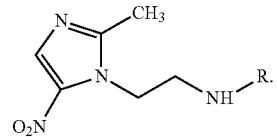

Formula 1

R = Asp; Glu; Asn; Gln; Gly; Ser; Lys; Cys; (Cys)$_2$; Arg comprising 1-(2-aminoethyl)-2 methyl-5-nitroimidazole or its derivatives connected with amino acids via chemical bonds.

The compound is served as a Chelan and is chelate with a nuclide to form a chelate complex and thus nuclear hypoxia contrast medium.

The nitroimidazole component of the compound targets hypoxic cells. The mechanism is that the R—NO$_2$ group is converted into R—NH$_2$ by Nitroreductase in hypoxic cells (FIG. 1). Due to this bio-chemical reaction which is specific to hypoxic cells, the contrast medium of the current invention can be accumulated inside hypoxic cells. The contrast medium molecule of the current invention contains amino acid component, which possesses negatively charged R—COO$^-$ and —NH$_2$ groups. These groups can easily chelate positively charged radioactive nuclide and enables the whole molecule to be radioactive and thus tumors can be imaged by tracing radioactive nuclides.

There are two mechanisms of the tumor-targeting effect of the contrast medium of the current invention: 1). the rapid growth of tumor cells results in a lack of blood and oxygen supply to the central part of the tumor, and this leads to the formation of hypoxic and necrotic tissues. Due to the presence of the hypoxic tissue in the tumor, the contrast medium of the current invention can be used to image tumors. 2). Normal cells can synthesize asparagine which is essential for the growth of the cells. Tumor cells do not have this function, and has to rely on eternal supply of asparagines. The contrast medium of the current invention contains asparagines, and therefore can be used in tumor imaging.

The contrast medium of the current invention is a novel hypoxic-cell-targeting contrast medium. This contrast medium can chelate radioactive nuclides generally used clinically, such as $^{99m}$Tc, $^{113}$In. After being injected into the human body, the contrast medium is specifically accumulated in hypoxia cells and tissues. Through SPECT (ECT) or γ-camera, hypoxia lesions can be traced and can be clearly imaged after data date processing on computers. Hence, the doctors can accurately diagnose the location, size, and the degree of malignancy of the hypoxia tissues. Medically, the hypoxia lesions mentioned above refer to certain tissues in human body which are lacking supply of oxygen and blood so that the cells and the tissues are dead (such as cerebral thrombosis, tumors, and other thrombosis).

The derivatives of the nitroimidazole of the invention have a formula as shown in Formula 2:

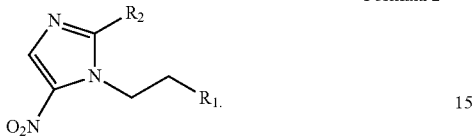

Formula 2

$R_1$ = $NH_2$; OH; COOH; SH; F; Cl; Br; I
$R_2$ = H; $CH_3$; $CH_2$—$CH_3$; $CH(CH_3)_2$; $NH_2$; F; Cl; Br; I; $SCH_3$; $SO_2CH_3$

The amino acids in the contrast medium of the current invention are aspartic acid (Asp), glutamic acid (Glu), asparagines (Asn), glutamine (Gln), glycine (Gly), serine (Ser), lysine (Lys), cysteine (Cys), cystine ($(Cys)_2$), or arginine (Arg), and they are D- or L-amino acids.

The amino acids connected with the nitroimidazole or their derivatives are 1 to 15 amino acids, and they are concatenated to one another as shown in Formula 3,

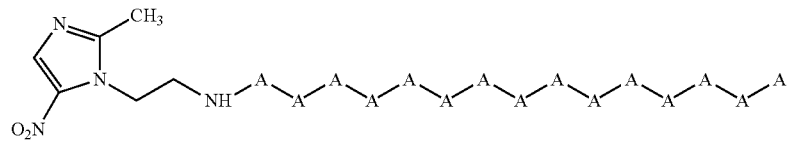

Formula 3

Amino acids (2-15) concatenated to one another or connected to another in parallel as shown in Formula 4,

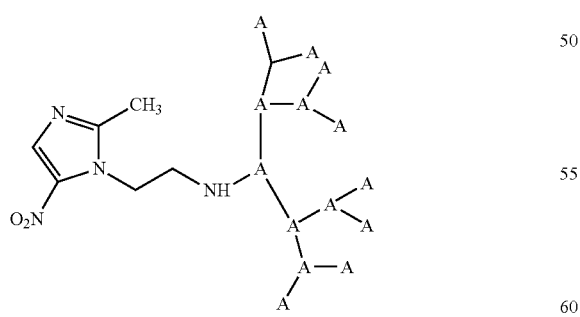

Formula 4

Amino acids (2-15) connected to one another in parallel or connected to one another both in an concatenated way and in parallel as shown in Formula 5, Formula 5

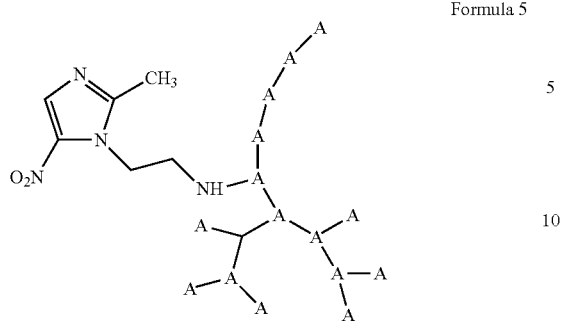

Amino acids (2-15) connected to other both in a concatenated way an in parallel wherein the compound contains only one kind of amino acid connected in a way as shown in Formula 6, Formula 6

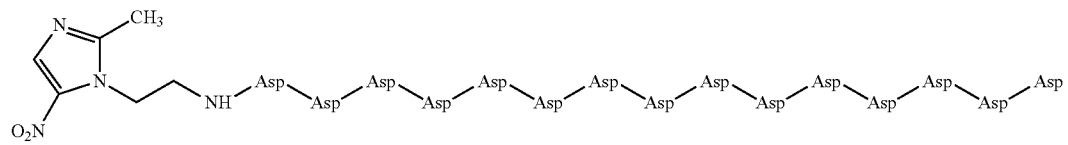

Single kind of amino acids (e.g. aspartic acid) arranged in concatenation or two kinds of amino acids cross connected to one another as shown in Formula 7, Formula 7

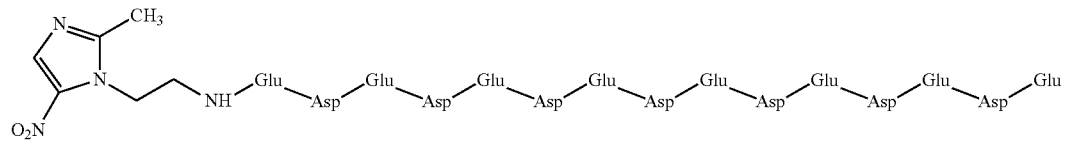

Two kinds of amino acids (e.g. glutamic acid and aspartic acid) cross connected to one another or any kind of amino acids arranged in a random way as shown in Formula 8.

Formula 8

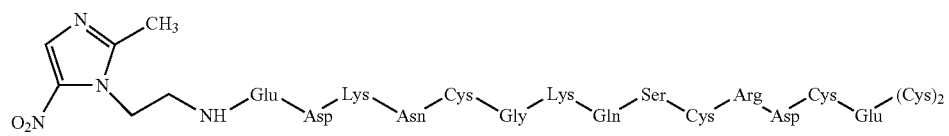

Multiple amino acids connected to one another in a random way

When the amino acid is aspartic acid or glutamic acid, the amino acid is connected with the nitroimidazole or the derivative of the nitroimidazole or with another amino acid through α carbon, or through β or γ carbon as shown in Formula 9.

Formula 9

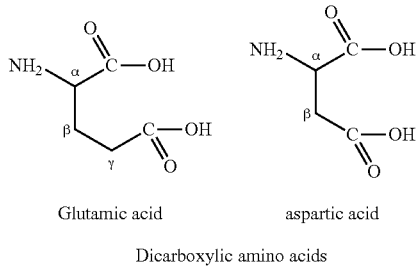

Glutamic acid      aspartic acid

Dicarboxylic amino acids

The radioactive nuclides used in the contrast medium of the current invention is $Tc^{99m}$, $In^{113m}$, $In^{111m}$, $I^{131}$, $P^{32}$, $Hg^{203}$, $Ga^{67}$, $Ga^{68}$, $Sr^{85}$, $Cr^{51}$, $Xe^{133}$, $Tl^{201}$, $Kr^{81m}$, $Rb^{86}$, $Rb^{86}$, or $Cu^{62}$.

The contrast medium is the compound in Formula 10,

Formula 10

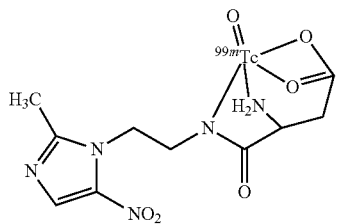

wherein the radioactive nuclide is chelate inside a single molecule, or the contrast medium is the compound in Formula 11, Formula 11

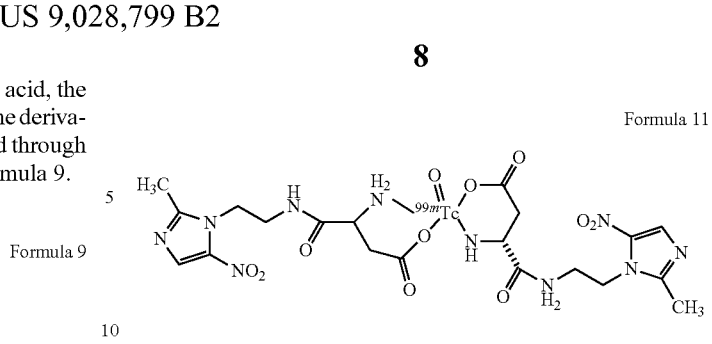

wherein the radioactive nuclide is chelate between two molecules.

Still in accordance with one embodiment of the invention, there provided is a method for preparation of the precursor of the nitroimidazole-amino acid nuclear hypoxia contrast medium.

The amino group (—NH$_2$—) of 1-(2-aminoethyl)-2 methyl-5-nitroimidazole is reacted with the carboxyl group of L-aspartic acid, a H$_2$O molecule is released and an amide group is formed and the reaction product is 1-(2-L-asparaginylethyl)-2 methyl-5-nitroimidazole (FW=285) (Formula 12), Formula 12

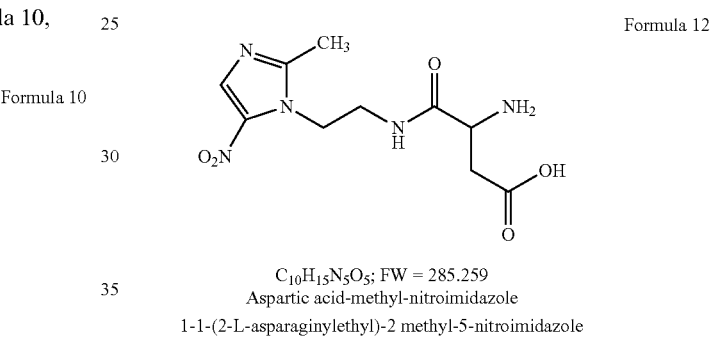

$C_{10}H_{15}N_5O_5$; FW = 285.259
Aspartic acid-methyl-nitroimidazole
1-1-(2-L-asparaginylethyl)-2 methyl-5-nitroimidazole and thus the contrast medium of the current invention is formed.

The process is described as Reaction 1.

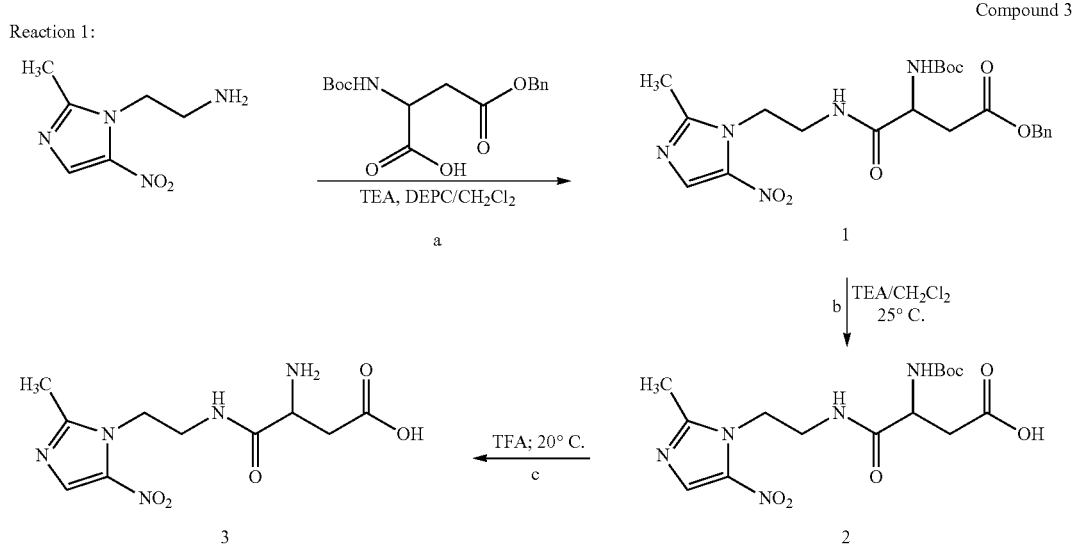

1-(2-L-asparaginylethyl)-2 methyl-5-nitroimidazole

A. Synthesis of Compound 1: (1-[2-(2-(isobutylamino)-4-benzyl-L-aspartic ester)acylamideethyl]-2 methyl-5-nitroimidazole 3-30 mmol 2-(isobutylamino)-4-benzyl-L-asparticester is dissolved 50-500 mL dry dichloromethane solution. 3-30 mmol triethylamine, 3-30 mmol 1-(2-aminoethyl)-2 methyl-5-nitroimidazole and 3-30 mmol phosphoryl cyanide are added sequentially at room temperature into the dichloromethane solution. The solution is stirred simultaneously. The reaction mixture is washed with 100-120 mL water and dried with $MgSO_4$. The final products are separated using silica gel column. Dichloromethane and ethanol are in the mobile phase in a volume ratio of 4:1. The obtained product is (1-[2-(2-(isobutylamino)-4-benzyl-L-aspartic ester)acylamideethyl]-2 methyl-5-nitroimidazole.

B. Synthesis of Compound 2: (1-[2-(2-(isobutylamino)-L-aspartic acid)acylamideethyl]-2 methyl-5-nitroimidazole 1-30 mmol the compound 1 is dissolved in 10-300 mL dry dichloromethane solution. 5-30 mmol Triethylamine and 1-30 mmol phosphoryl cyanide are added sequentially and the reaction mixture is stirred for 12-18 hours. 50-500 mL dichloromethane is added into the solution. The reaction mixture is washed with 100 mL water and dried with $MgSO_4$. The final products are separated using silica gel column. Dichloromethane and ethanol are in the mobile phase in a volume ratio of 4:1. The obtained product is (1-[2-(2-(isobutylamino)-L-aspartic acid)acylamideethyl]-2 methyl-5-nitroimidazole.

C. Synthesis of Compound 3: 1-(2-L-asparaginylethyl)-2 methyl-5-nitroimidazole 1-30 mmol the compound 2 is dissolved in 1-300 mL trifluoacetic acid. The mixture is stirred at room temperature for 20-30 min. Extra trifluoacetic acid is removed and 5-10 mL hexane is added to remove a small amount of trifluoacetic acid. The reaction product is dissolved in 10-300 mL water. The pH value is the adjusted to 9. The reaction product 3 1-(2-L-asparaginylethyl)-2 methyl-5-nitroimidazole separated is re-crystallized in a mixture of water:ethanol of 1:1.

The chemical reactions of the current invention are simple. The final product (aspartic acid-methyl-nitroimidazole) (FIGS. 2, 3, 4) has a high yield. The purification method is also very simple. The raw product (aspartic acid-methyl-nitroimidazole) has a purity of 95%. After being chelate with radioactive nuclides, the product has a high radioactivity (FIG. 5).

Still in accordance with one embodiment of the invention, there provided is a method to apply the nitroimidazole-amino acid nuclear hypoxia contrast medium in the production of the imaging contrast medium.

A further goal of the current invention is apply the nitroimidazole-amino acid nuclear hypoxia contrast medium in the diagnosis of malignant tumors, evaluation after tumor operation or treatment, and the brain scan of cerebral hypoxia caused by cerebral thrombosis.

For example: (1) cerebral thrombosis: Cerebral thrombosis leads to hypoxia and thus death of cerebral cells. This so caused stroke is very normal in middle aged and older people. Early clinic detection of the disease provides a time window for the treatment of the disease and is very crucial for the prognosis of the patients. Clinically, using CT and MRI to detect cerebral thrombosis and cerebral apoplexy at an early stage is very difficult and the clinical treatment of these two diseases is very different. The contrast medium of the current invention is functional contrast medium, and therefore it can detect these two brain diseases at an early stage. In addition, the contrast medium of the current invention can also trace the prognosis of the patients after they have been treated.

(2) Tumors: The rapid growth of tumor cells results in a lack of blood and oxygen supply to the central part of the tumor, and this leads to the formation of hypoxic and necrotic tissues. The contrast medium of the current invention has a great imaging effect for tumor cells and is very sensitive for tumor imaging (it can image tumor with a size more than 1.5 cm). 3D tumor images can be obtained via SPECT (ECT), which facilitates an early detection of the location, size and degree of malignancy of the tumor. Furthermore, the contrast medium of the current invention can also be used to image the tumor on a regular basis and the images can be used to trace and evaluate the effect of the treatment as well as the resistance of the tumors against the treatment.

The contrast medium of the current invention can be used in imaging cerebral thrombosis, tumors or other diseases such as ulceration, thrombosis, etc.

There are two mechanisms of the tumor-targeting effect of the contrast medium of the current invention: 1). the rapid growth of tumor cells results in a lack of blood and oxygen supply to the central part of the tumor, and this leads to the formation of hypoxic and necrotic tissues. Due to the presence of the hypoxic tissue in the tumor, the contrast medium of the current invention can be used to image tumors. 2). Normal cells can synthesize asparagine which is essential for the growth of the cells. Tumor cells do not have this function, and has to rely on eternal supply of asparagines. The contrast medium of the current invention contains asparagines, and therefore can be used in tumor imaging.

The contrast medium of the current invention is a novel hypoxic-cell-targeting contrast medium. This contrast medium can chelate radioactive nuclides generally used clinically, such as $^{99m}Tc$, $^{113m}In$. After being injected into the human body, the contrast medium is specifically accumulated in hypoxia cells and tissues. Through SPECT (ECT) or γ-camera, hypoxia lesions can be traced and can be clearly imaged after data processing on computers. Hence, the doctors can accurately diagnose the location, size, and the degree of malignancy of the hypoxia tissues. Medically, the hypoxia lesions mentioned above refer to certain tissues in human body which are lacking supply of oxygen and blood so that the cells and the tissues are dead (such as cerebral thrombosis, tumors, and other thrombosis).

Therefore, the contrast medium of the current invention can be used in the diagnosis of malignant tumors, evaluation after tumor operation or treatment, and the brain scan of cerebral hypoxia caused by cerebral thrombosis.

The method to produce the contrast medium of the current invention is simple and convenient, and has a high clinic application value.

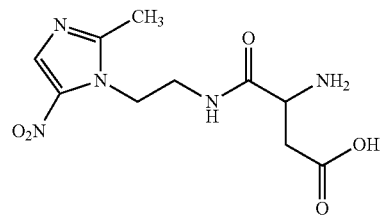

Formula 12

$C_{10}H_{15}N_5O_5$; FW = 285.259
Aspartic acid-methyl-nitroimidazole
1-1-(2-L-asparaginylethyl)-2 methyl-5-nitroimidazole and thus the contrast medium of the current invention is formed. The reaction step (Reaction 1) is very simple.

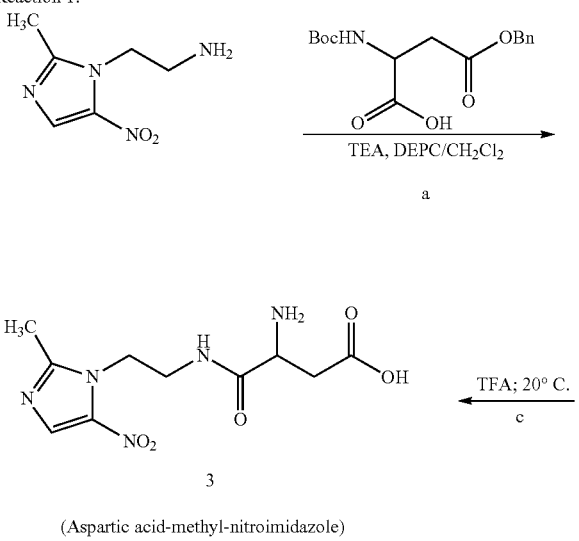

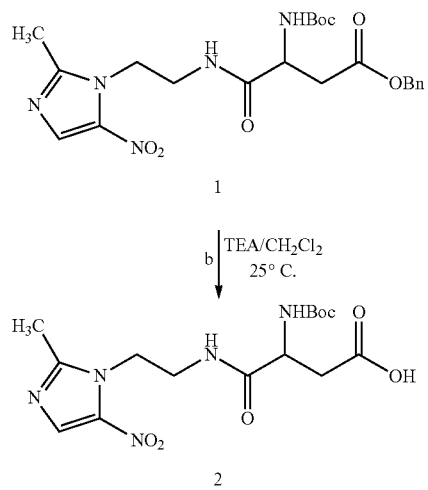

(Aspartic acid-methyl-nitroimidazole)

$^{99m}$Tc L-aspartic acid (T/M=1.1)
$^{99m}$Tc L-aspartic acid-methyl-nitroimidazole (T/M=4.3)
$^{99m}$Tc L-aspartic acid (T/M=2.5)
$^{99m}$Tc L-aspartic acid-methyl-nitroimidazole (T/M=3.7)

Figure 13:
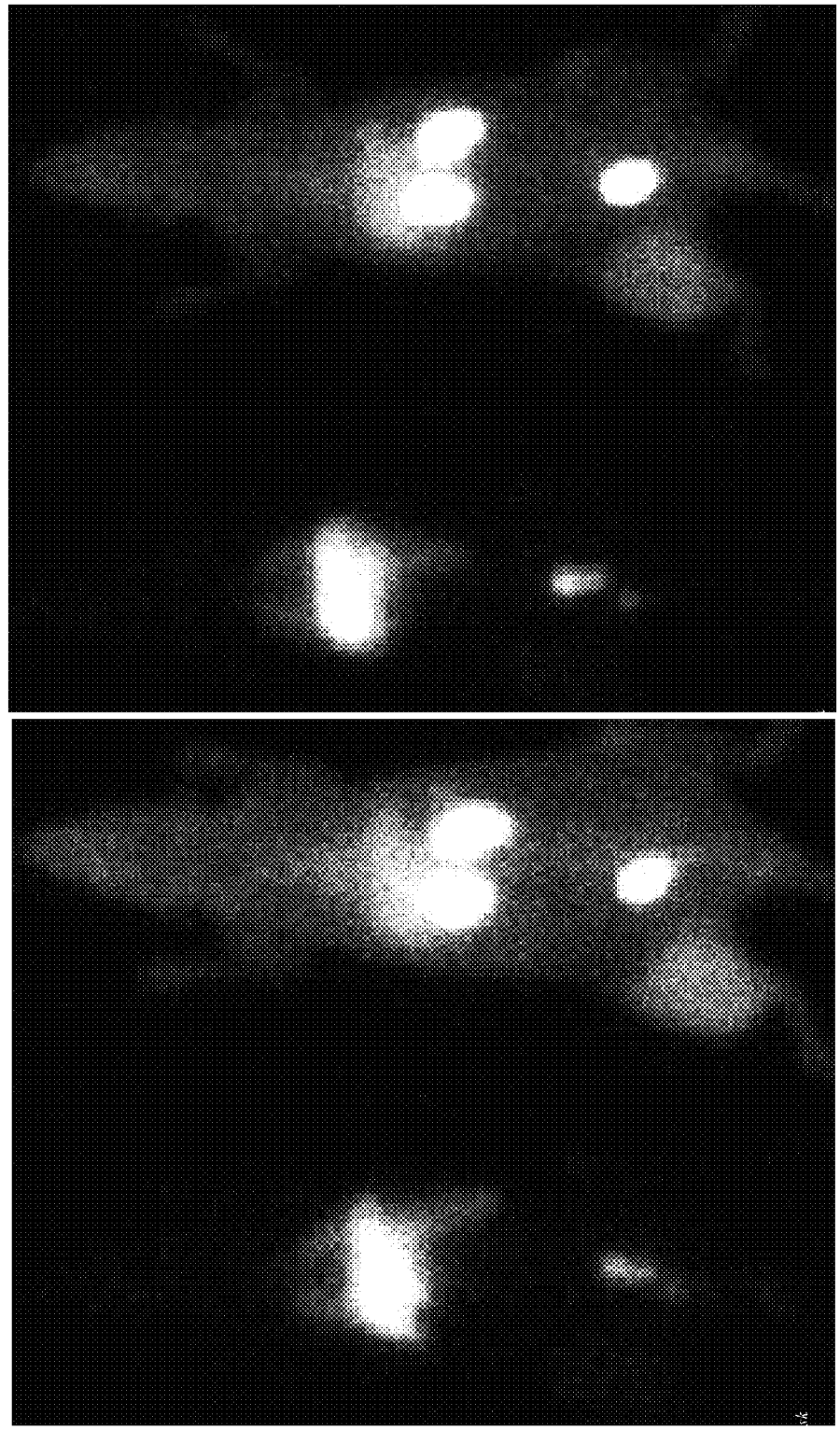

FIG. 13 the image of mice (with breast cancer cells on the legs) on γ-camera after the nuclide contrast medium is intravenous injected.

$^{99m}$Tc L-aspartic acid (T/M=2.2)
$^{99m}$Tc L-aspartic acid-methyl-nitroimidazole (T/M=4.3)
$^{99m}$Tc L-aspartic acid (T/M=1.5)
$^{99m}$Tc L-aspartic acid-methyl-nitroimidazole (T/M=4.1)

DETAILED DESCRIPTION OF THE EMBODIMENTS

Example 1

Figure 1:
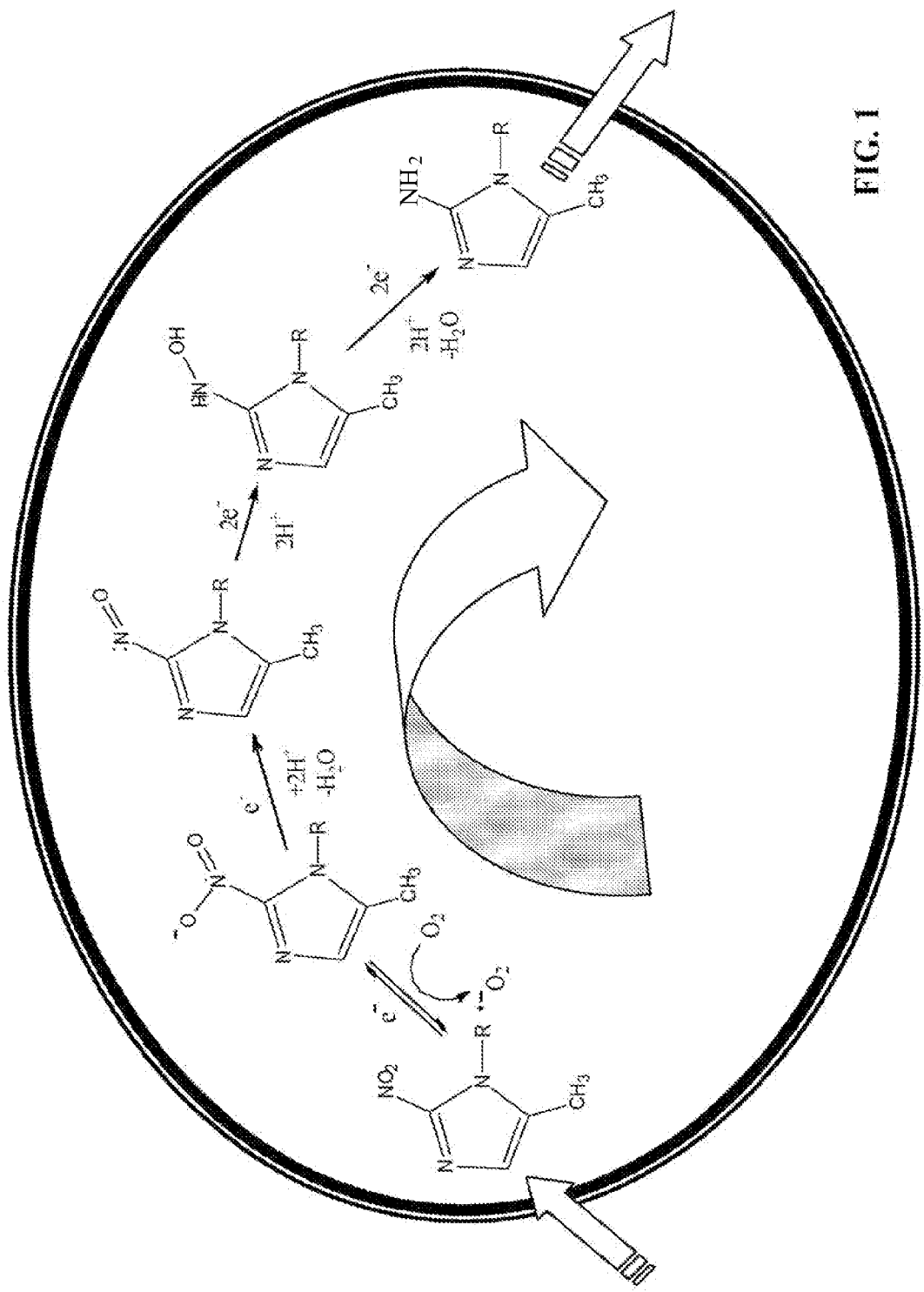
FIG. 1 the conversion of the R—$NO_2$ group of the nitroimidazole molecule into R—$NH_2$ group in hypoxic cells.
Figure 2:
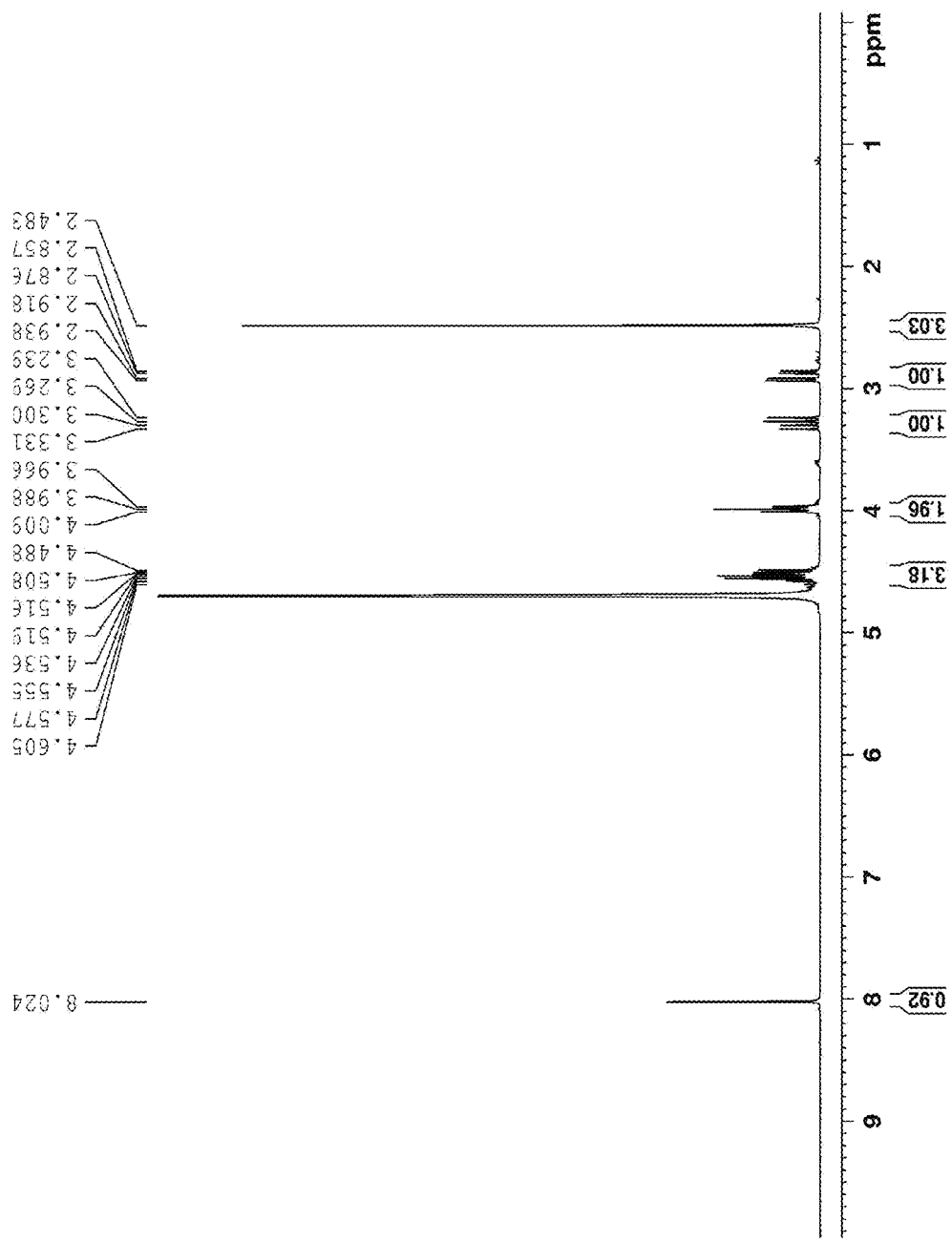
FIG. 2 $^1$H-NMR spectroscopy of the final reaction product aspartic acid-methyl-nitroimidazole.
Figure 3:
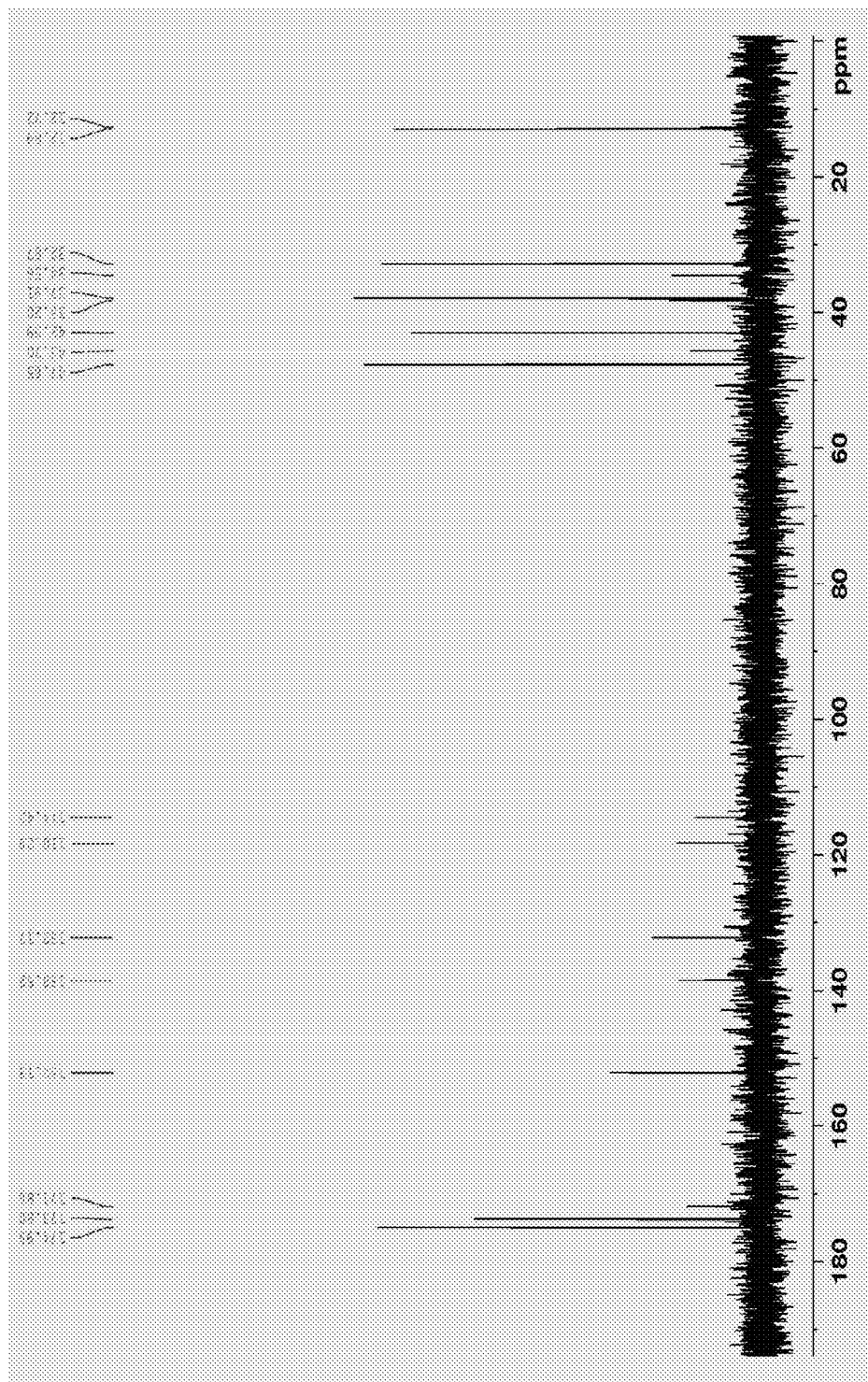
FIG. 3 $^{13}$C-NMR spectroscopy of the final reaction product aspartic acid-methyl-nitroimidazole.
Figure 4:
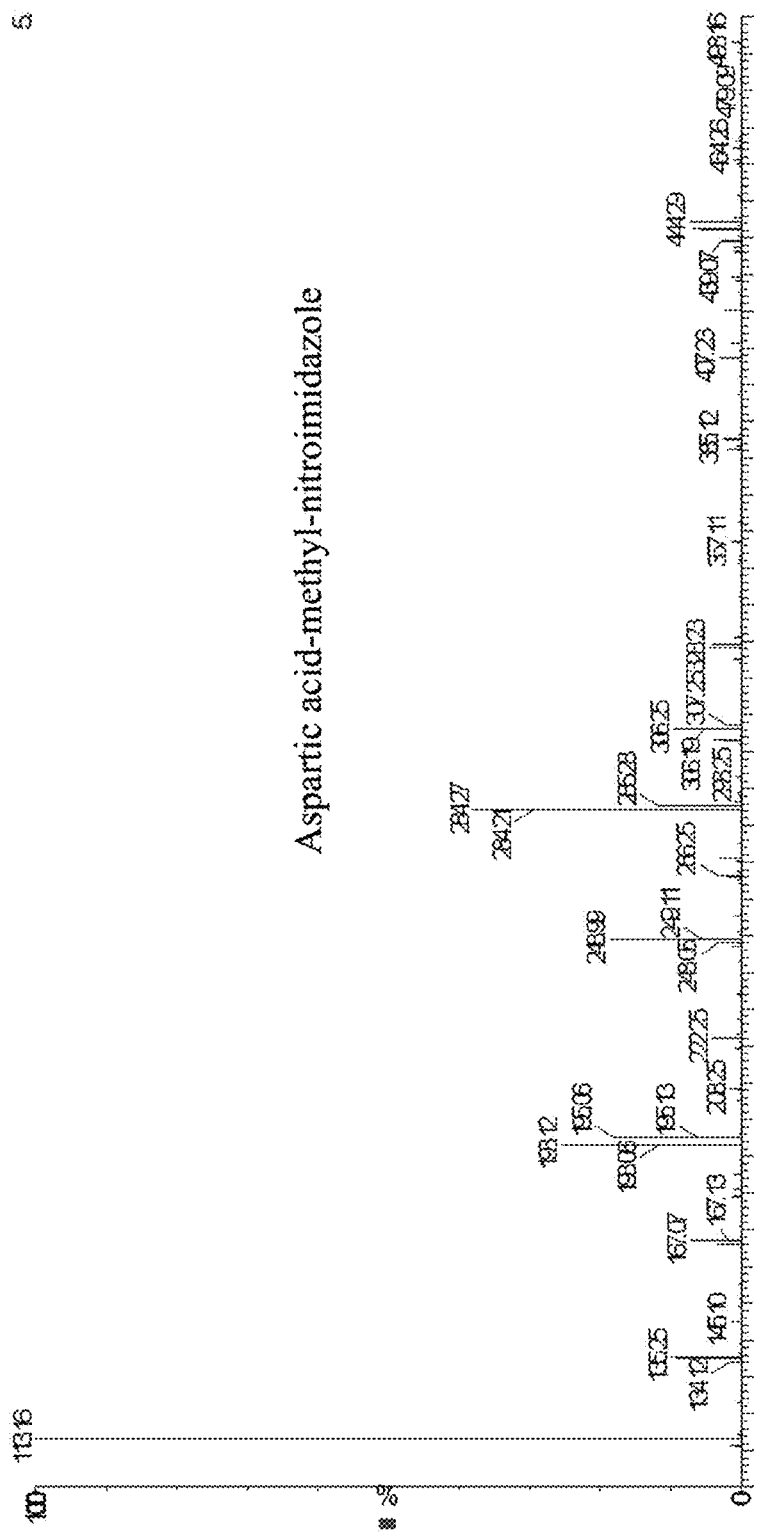
FIG. 4 mass spectroscopy (MS) of the final reaction product aspartic acid-methyl-nitroimidazole.
Figure 5:
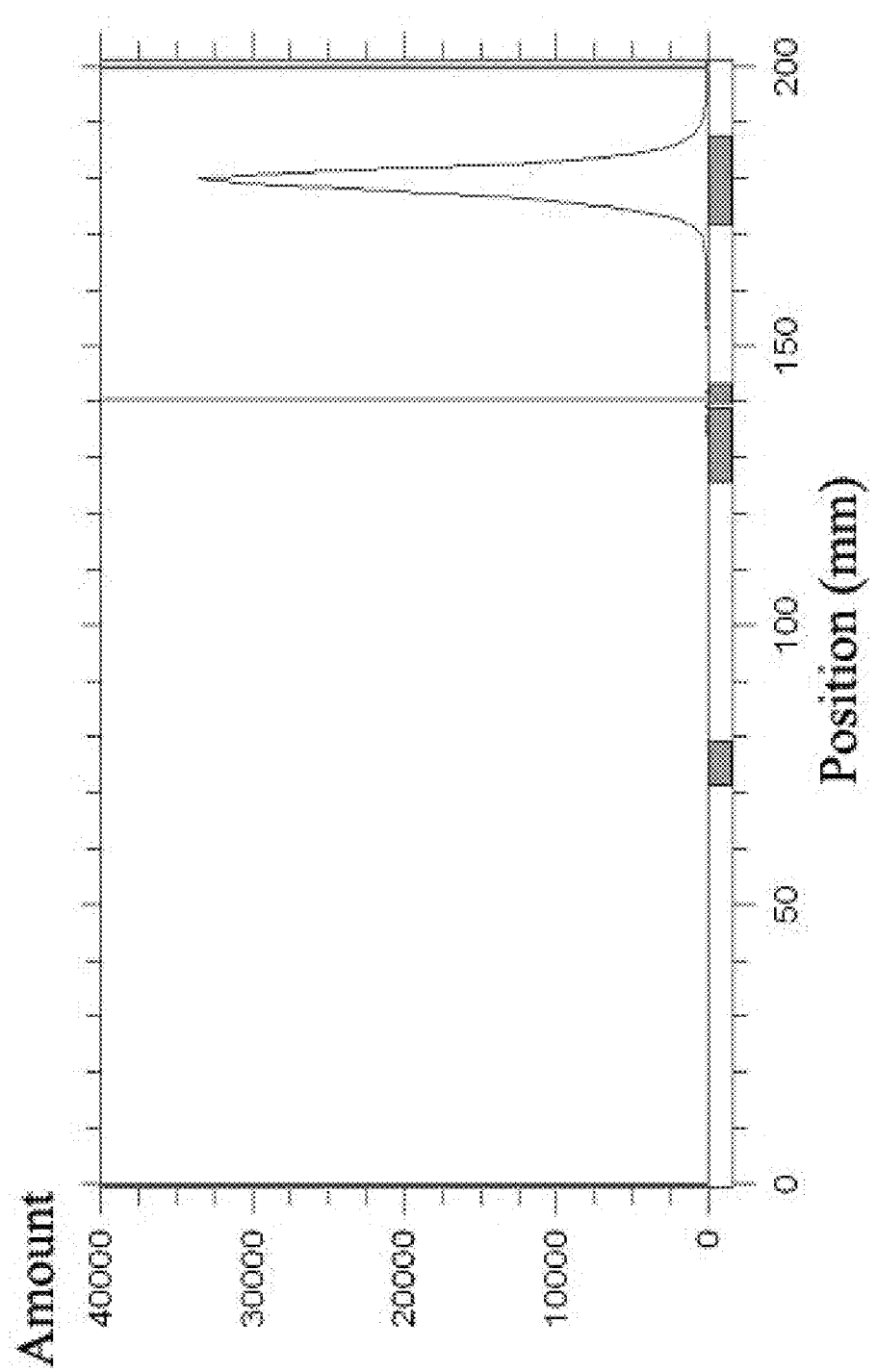
FIG. 5 radioactive TLC diagram of $^{99m}$Tc aspartic acid-methyl-nitroimidazole.

The amino group (—NH$_2$—) of 1-(2-aminoethyl)-2 methyl-5-nitroimidazole is reacted with the α carboxyl group (—COOH) of L-aspartic acid, a H$_2$O molecule is released and an amide group is formed and the reaction product is 1-(2-L-asparaginylethyl)-2 methyl-5-nitroimidazole (FW=285) (Formula 12), The yield of the final product (MNA) (FIGS. 2, 3, 4) is pretty high (73%), and is easy to purify. The purity of the raw product (aspartic acid-methyl-imidazole) can reach 95%, and after it is chelate with the radioactive nuclide, the radioactivity is high (FIG. 5).

A. Synthesis of Compound 1: (1-[2-(2-(isobutylamino)-4-benzyl-L-aspartic ester)acylamideethyl]-2 methyl-5-nitroimidazole 3.2 g, 10.0 mmol 2-(isobutylamino)-4-benzyl-L-asparticester is dissolved in 100 mL dry dichloromethane solution. 4.2 mL (30.0 mmol) Triethylamine, 10.0 mmol (2.6 g) 1-(2-aminoethyl)-2 methyl-5-nitroimidazole and 1.7 mL (10.0 mmol) phosphoryl cyanide are added sequentially at room temperature into the dichloromethane solution. The solution is stirred for 2 hours. 100 mL dichloromethane is then added into the mixture. The reaction mixture is washed with water twice (50-60 mL each time) and dried with MgSO$_4$. The final products are separated using silica gel column. Dichloromethane and ethanol are in the mobile phase in a volume ratio of 4:1. 3.7 g (1-[2-(2-(isobutylamino)-4-benzyl-L-aspartic ester)acylamideethyl]-2 methyl-5-nitroimidazole is obtained (product yield: 80.6%).

B. Synthesis of Compound 2: (1-[2-(2-(isobutylamino)-L-aspartic acid)acylamideethyl]-2 methyl-5-nitroimidazole 20 g (4.4 mmol) the compound 1 is dissolved in 30 mL dry dichloromethane solution. 1.8 mL (13.2 mmol) triethylamine and 0.7 mL (4.4 mmol) phosphoryl cyanide are added sequentially and the reaction mixture is stirred for 12-18 hours. 100 mL dichloromethane is added into the solution. The reaction mixture is washed with water twice (50 mL each time) and dried with $MgSO_4$. The final products are separated using silica gel column. Dichloromethane and ethanol are in the mobile phase in a volume ratio of 4:1. 1.5 g (1-[2-(2-(isobutylamino)-L-aspartic acid)acylamideethyl]-2 methyl-5-nitroimidazole is obtained (product yield: 93.5%).

C. Synthesis of Compound 3: 1-(2-L-asparaginylethyl)-2 methyl-5-nitroimidazole 1.7 g (5.0 mmol) the compound 2 is dissolved in 4.0 mL trifluoacetic acid. The mixture is stirred at room temperature for 20-30 min. Extra trifluoacetic acid is removed and a small amount of hexane is added (twice, 5-10 mL each time) to removed a small amount of trifluoacetic acid. The reaction product is dissolved in 50 mL water. The pH value is the adjusted to 9. 1.3 g reaction product 3 1-(2-L-asparaginylethyl)-2 methyl-5-nitroimidazole separated is re-crystallized in a water:ethanol 1:1 solution (product yield: 91.5%).

Example 2

The amino group ($-NH_2-$) of 1-(2-aminoethyl)-2-methyl-5-nitroimidazole is reacted with the α carboxyl group ($-COOH$) of L-aspartic acid, a $H_2O$ molecule is released and an amide group is formed. After that, the other carboxyl group ($-COOH$) of the L-aspartic acid molecule is reacted with the amino group ($-NH_2-$) of another L-aspartic acid molecule, a $H_2O$ molecule is released and another amide group is formed. This contrast medium has two L-aspartic acid molecules connected to each other (Formula 13).

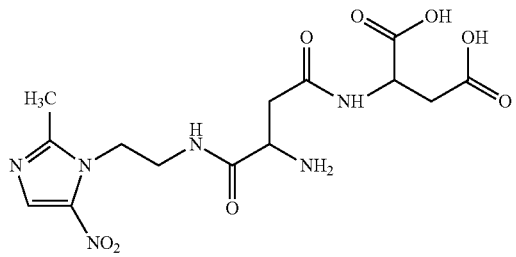

Formula 13

$C_{14}H_{20}N_6O_8$; FW = 400.35 Aspartic acid-aspartic acid-methyl-nitroimidazole
1-(2-L-asparaginyl(β-L-asparaginyl)ethyl)-2-methyl-5-nitroimidazole The reaction step is shown as follows (reaction 2).

Reaction 2

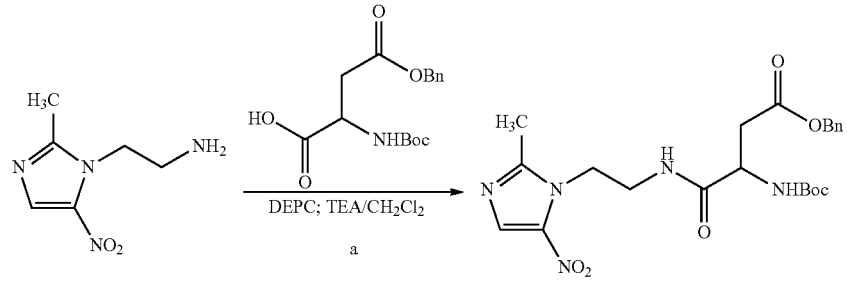

Compound 5

-continued

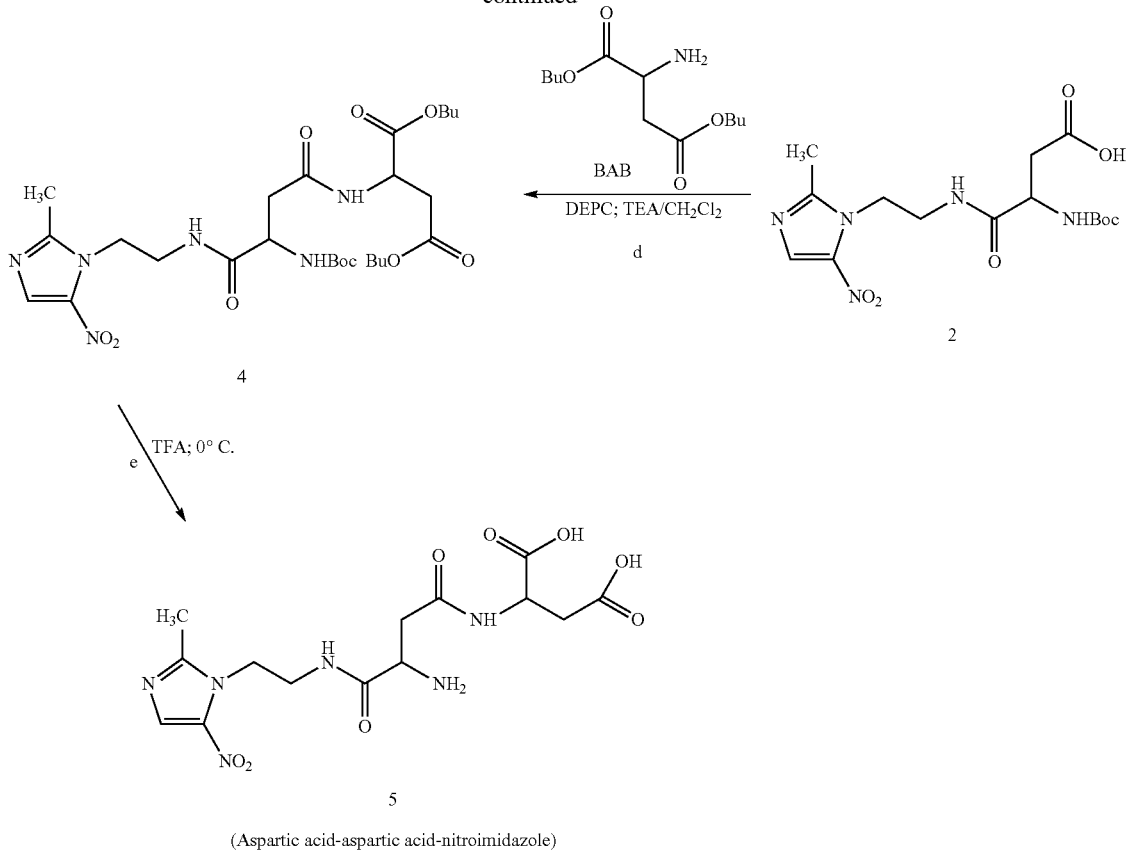

(Aspartic acid-aspartic acid-nitroimidazole)

Figure 6:
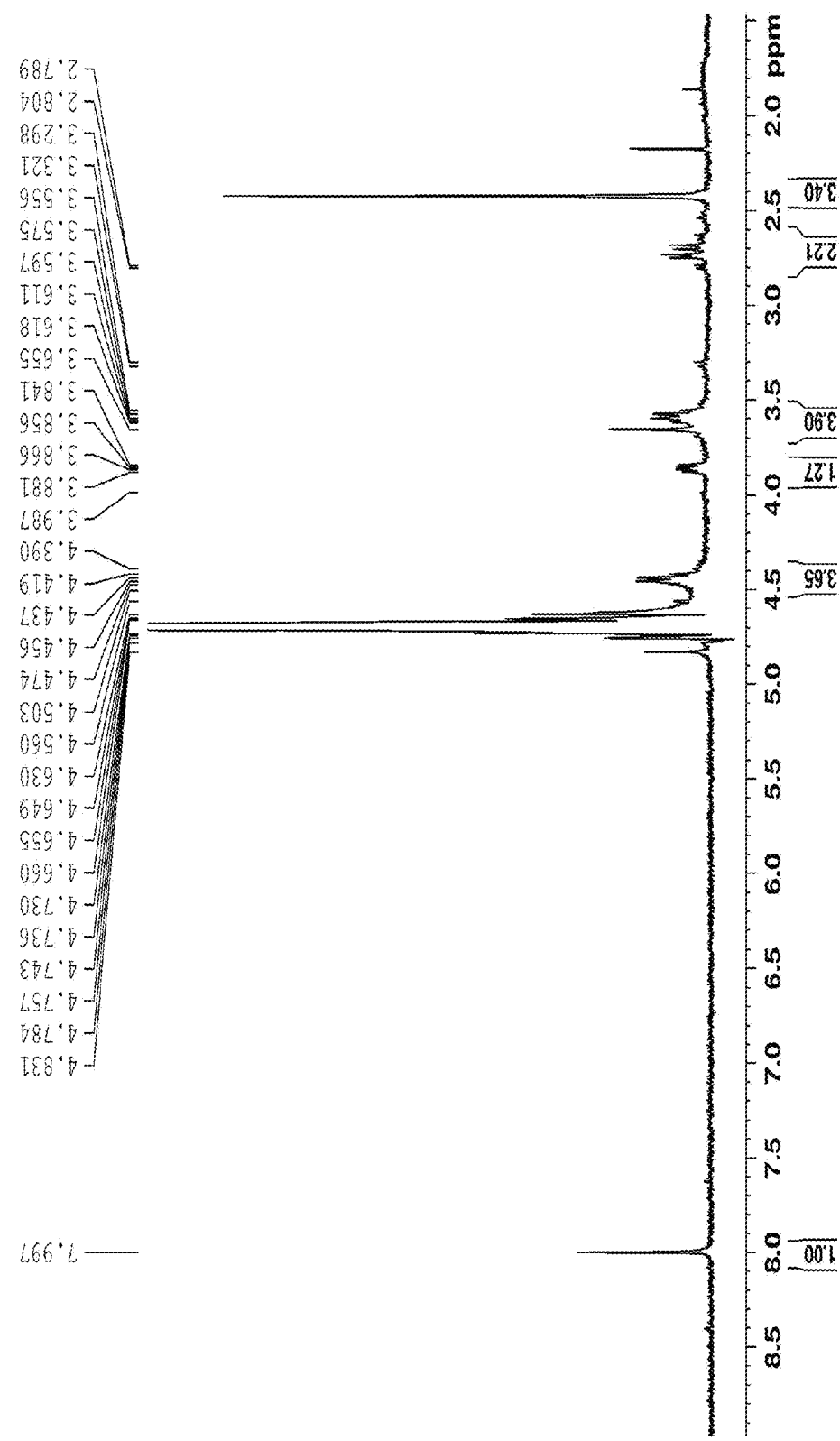
FIG. 6 $^1$H-NMR spectroscopy of the final reaction product aspartic acid-aspartic acid-methyl-nitroimidazole.
Figure 7:
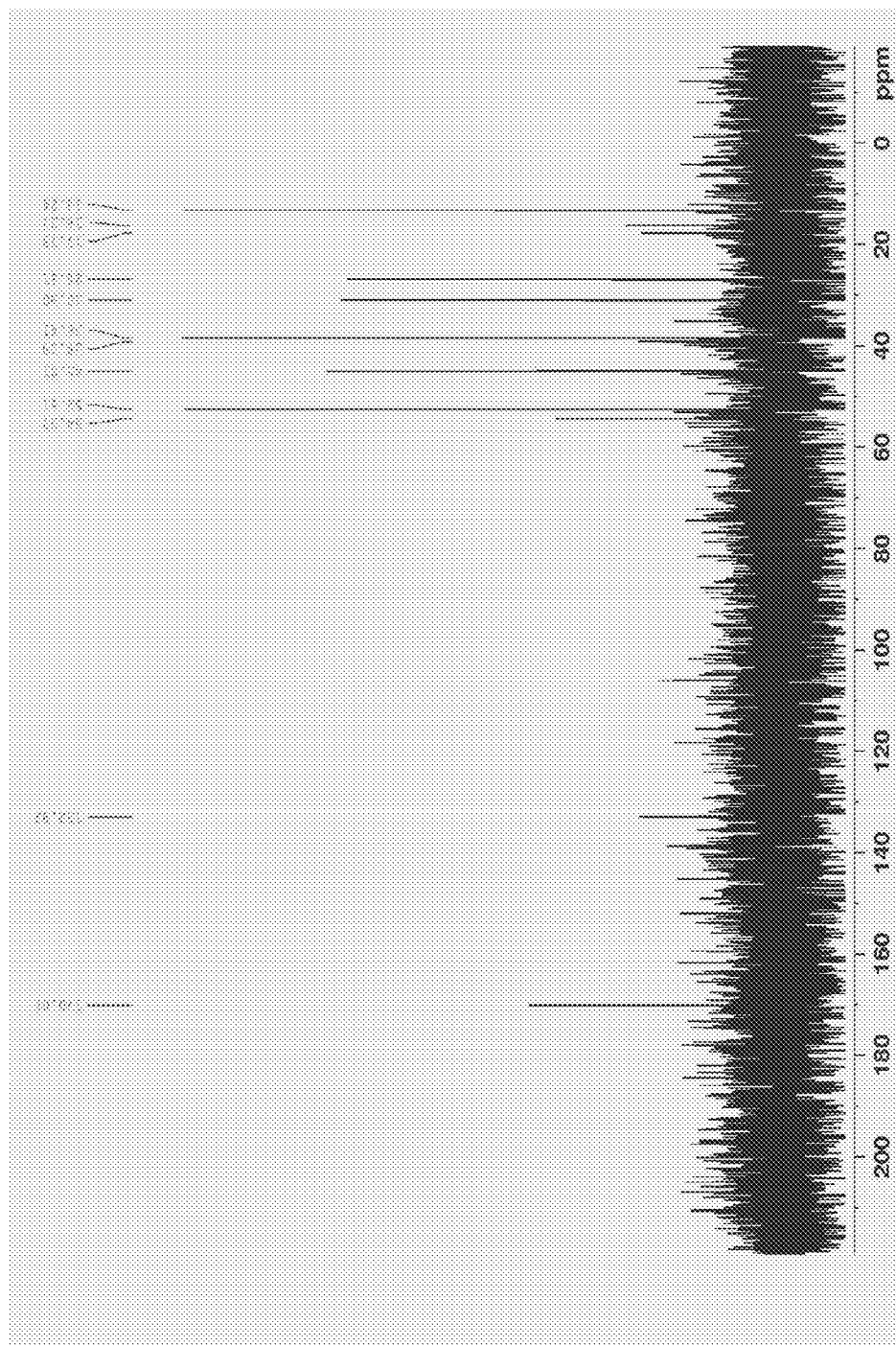
FIG. 7 $^{13}$C-NMR spectroscopy of the final reaction product aspartic acid-aspartic acid-methyl-nitroimidazole.
Figure 8:
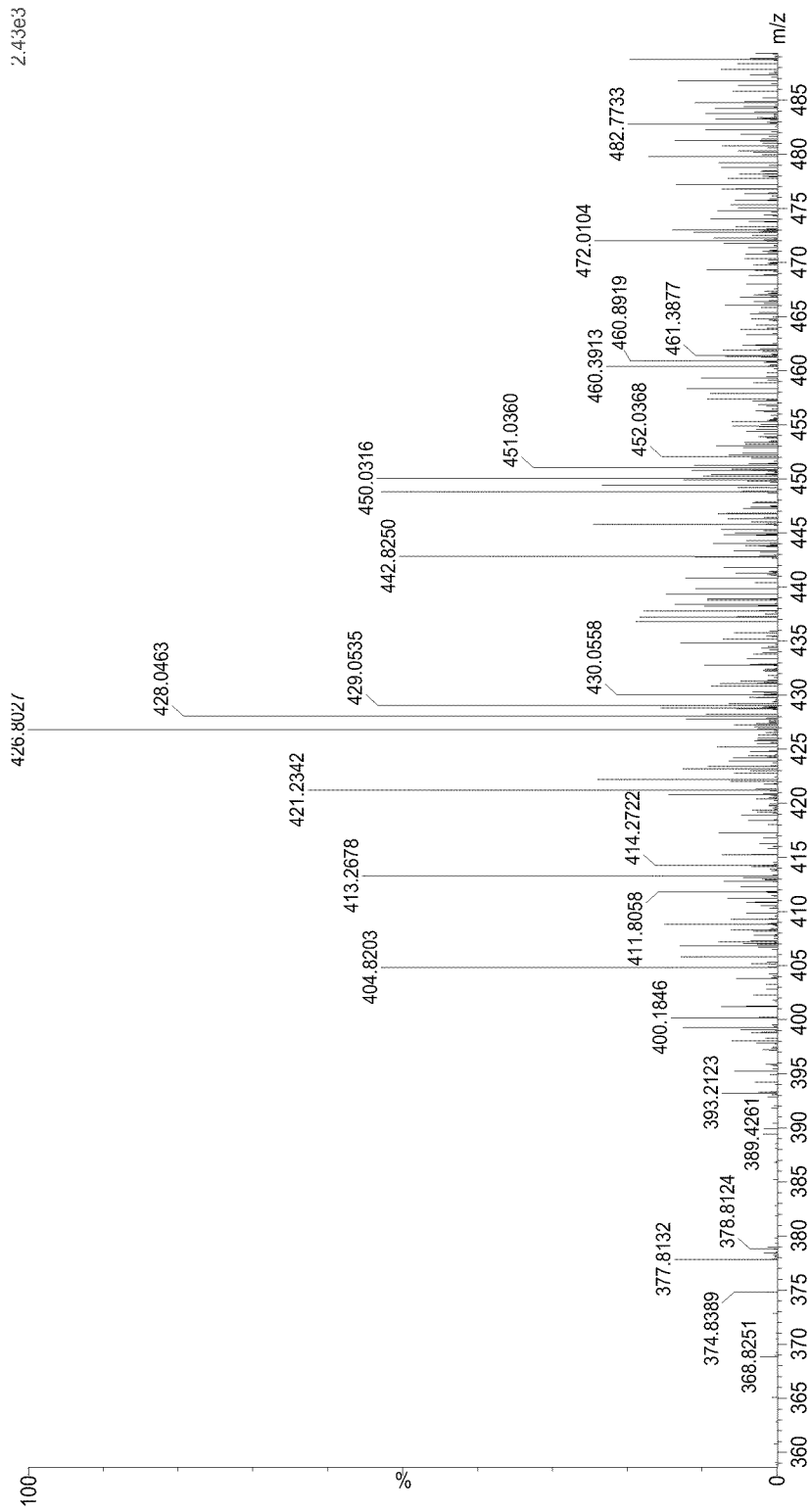
FIG. 8 mass spectroscopy (MS) of the final reaction product aspartic acid-methyl-nitroimidazole.

The final products (FIGS. 6, 7, 8) have yield of (75%). The purification method is easy. The raw product (aspartic acid-aspartic acid-methyl-nitroimidazole) has a purity of higher than 90%.

D. Synthesis of Compound 4

0.4 g (1.0 mmol) the compound 2 is dissolved in 10.0 mL dry trifluoacetic acid. 0.7 mL triethylamine (5.0 mmol), 0.3 g hydrochloric acid ditertiarybutyl-L-aspartic ester (1.0 mmol) and 0.2 mL phosphoryl cyanide are added sequentially at room temperature into the dichloromethane solution. The solution is stirred for 12 hours. 20 mL dichloromethane is then added into the mixture. The reaction mixture is washed with water twice (20-30 mL each time) and dried with MgSO$_4$. The final products are separated using silica gel column. Dichloromethane and ethanol are in the mobile phase in a volume ratio of 95:5. 0.48 g compound 4 is obtained (product yield: 79.2%).

E. Synthesis of Compound 5: (1-(2-L-asparaginyl(β-L-asparaginyl)ethyl)-2-methyl-5-nitroimidazole 1.5 g (2.5 mmol) the compound 4 is dissolved in 40 mL NaOH/ethanol solution (20 mL, 1.0 M NaOH and 20 mL ethanol) and the solution is stirred for 12 hours. The white solid product is filtered out and 0.85 g compound 5 ((1-(2-L-asparaginyl(β-L-asparaginyl)ethyl)-2-methyl-5-nitroimidazole is re-crystallized in 30 mL water and ethanol mixture solution (1:1) (yield is 85.2%).

Example 3

The amino group (—NH$_2$—) of 1-(2-aminoethyl)-2-methyl-5-nitroimidazole is reacted with the α carboxyl group (—COOH) of glutamic acid, a H$_2$O molecule is released and an amide group is formed. After that, the other carboxyl group (—COOH) of the L-glutamic acid molecule is reacted with the amino group (—NH$_2$—) of another L-aspartic acid molecule, a H$_2$O molecule is released and another amide group is formed. This contrast medium has one glutamic acid and one aspartic acid molecules connected to each other (Formula 14).

Formula 14

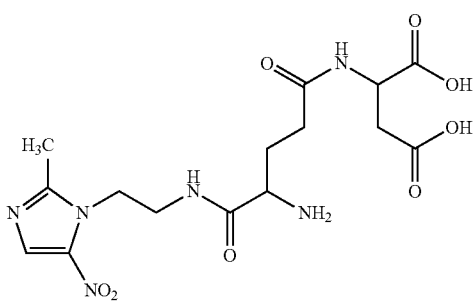

C$_{15}$H$_{22}$N$_6$O$_8$; FW = 414.37 Aspartic acid-glutamic acid-methyl-nitroimidazole
(1-(2-α-L-glutamine(β-L-asparaginyl)ethyl)-2-methyl-5-nitroimidazole The reaction step is shown as follows (reaction 3).

Reaction 3:

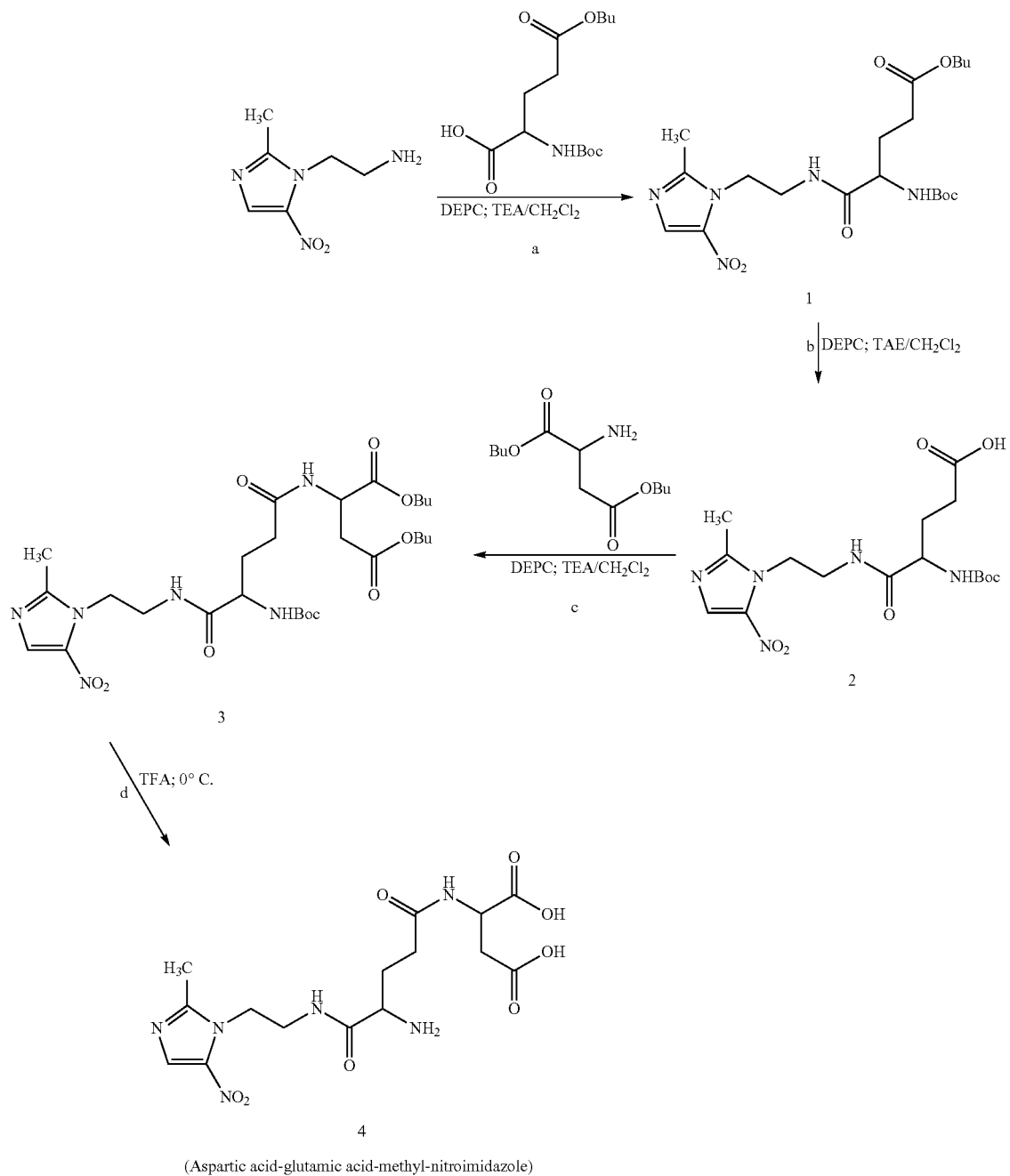

(Aspartic acid-glutamic acid-methyl-nitroimidazole)

Figure 9:
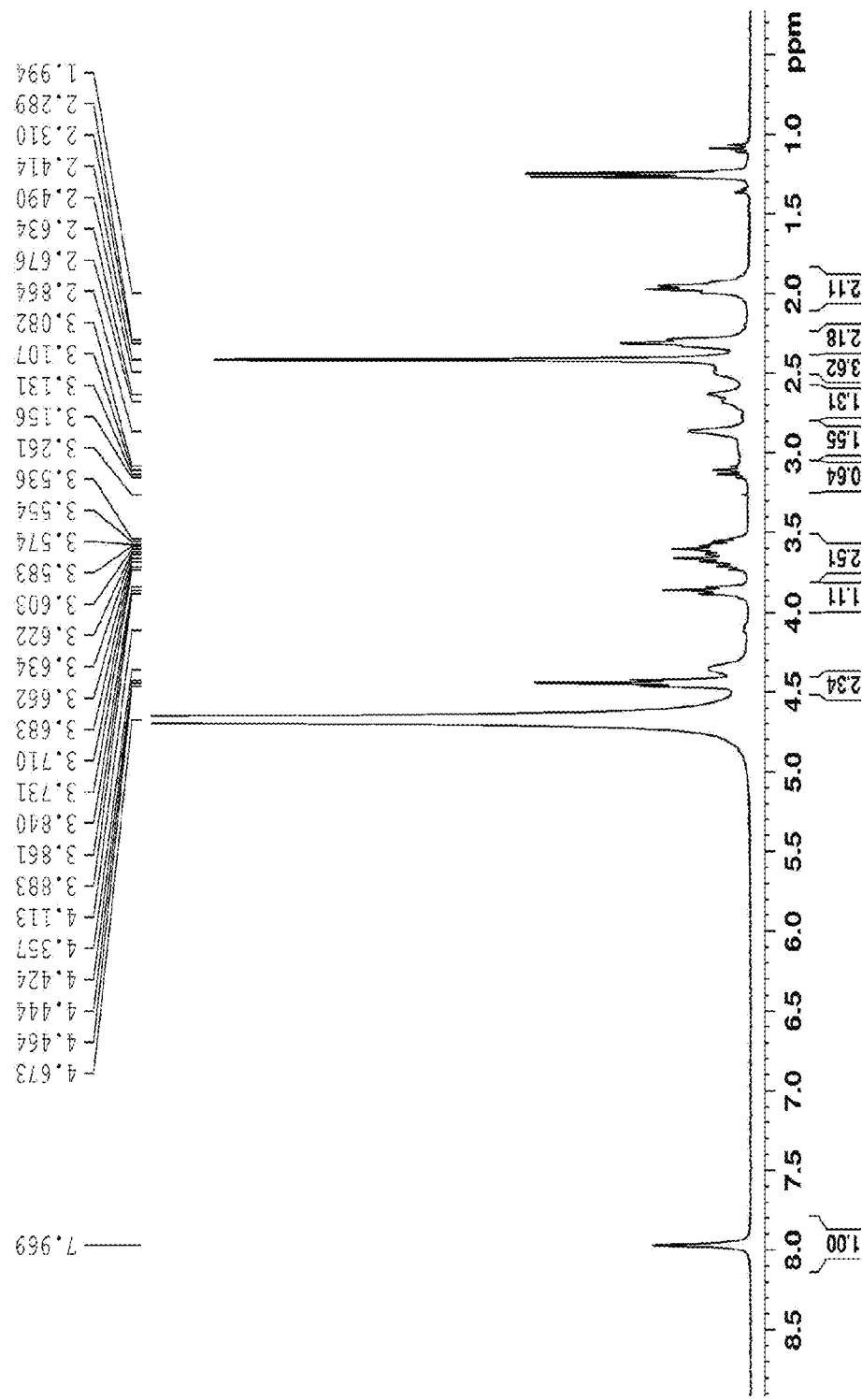
FIG. 9 $^1$H-NMR spectroscopy of the final reaction product aspartic acid-glutamic acid-methyl-nitroimidazole.
Figure 10:
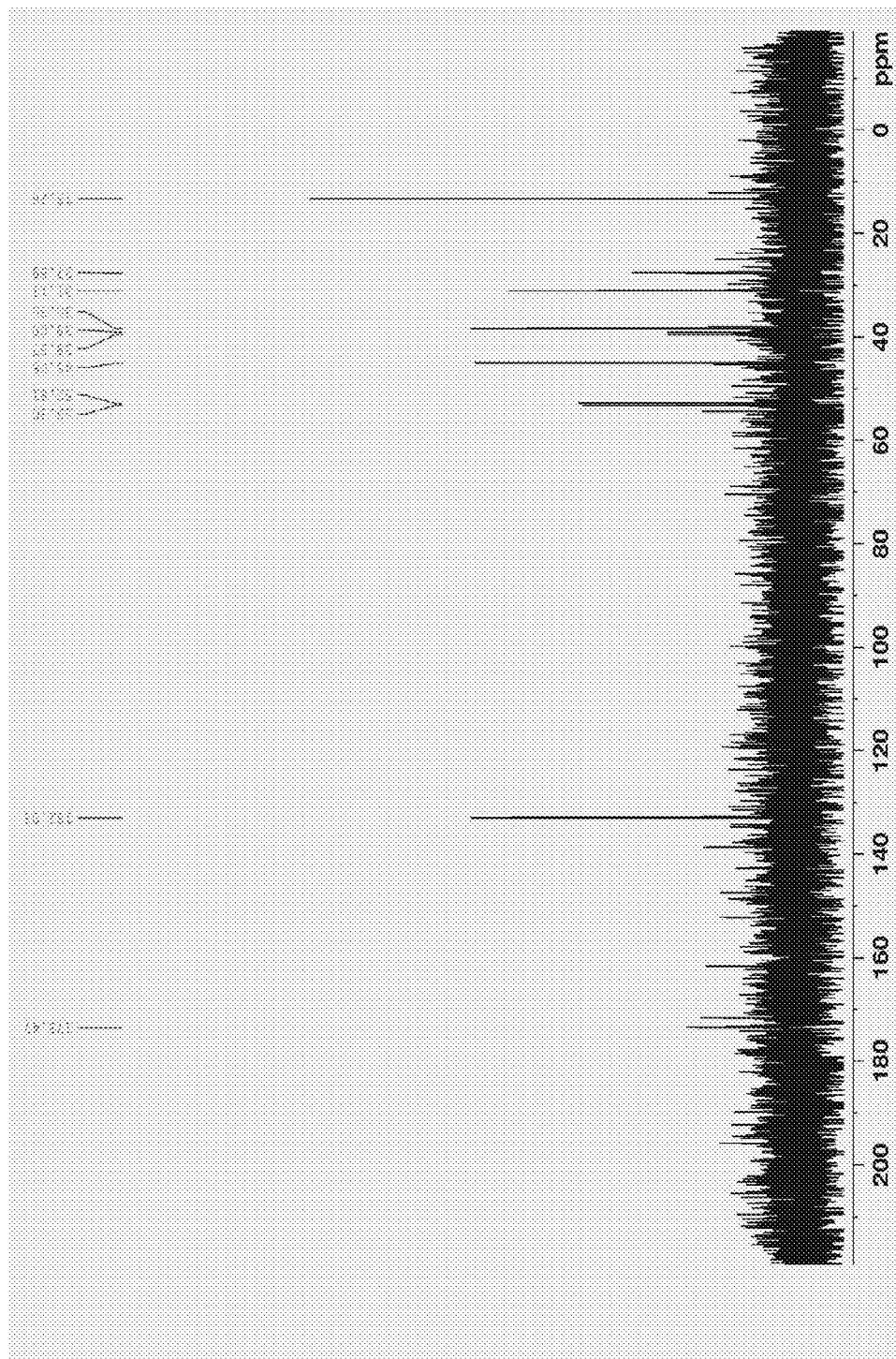
FIG. 10 $^{13}$C-NMR spectroscopy of the final reaction product aspartic acid-glutamic acid-methyl-nitroimidazole.
Figure 11:
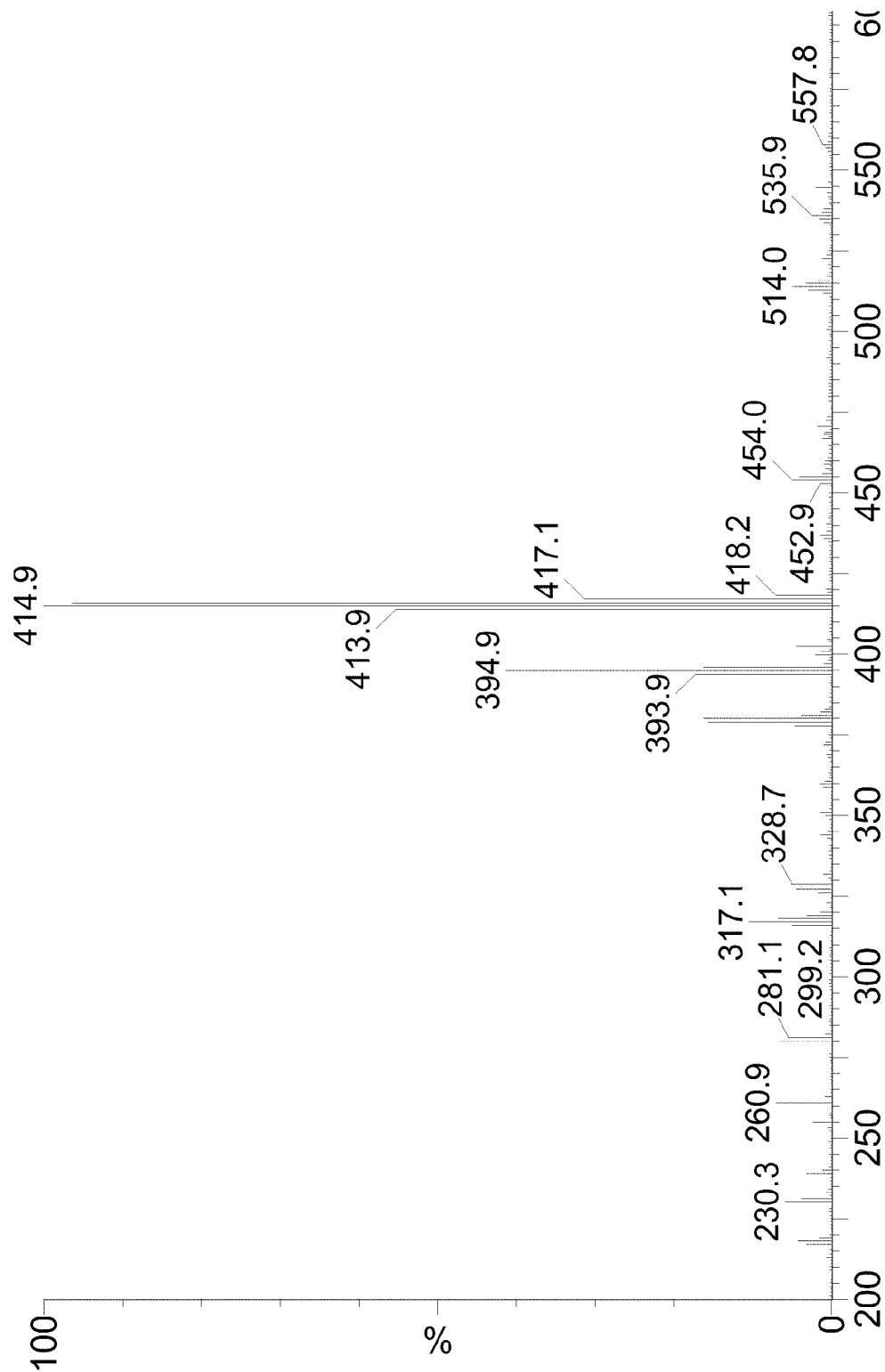
FIG. 11 mass spectroscopy (MS) of the final reaction product aspartic acid-glutamic acid-methyl-nitroimidazole.
Figure 12:
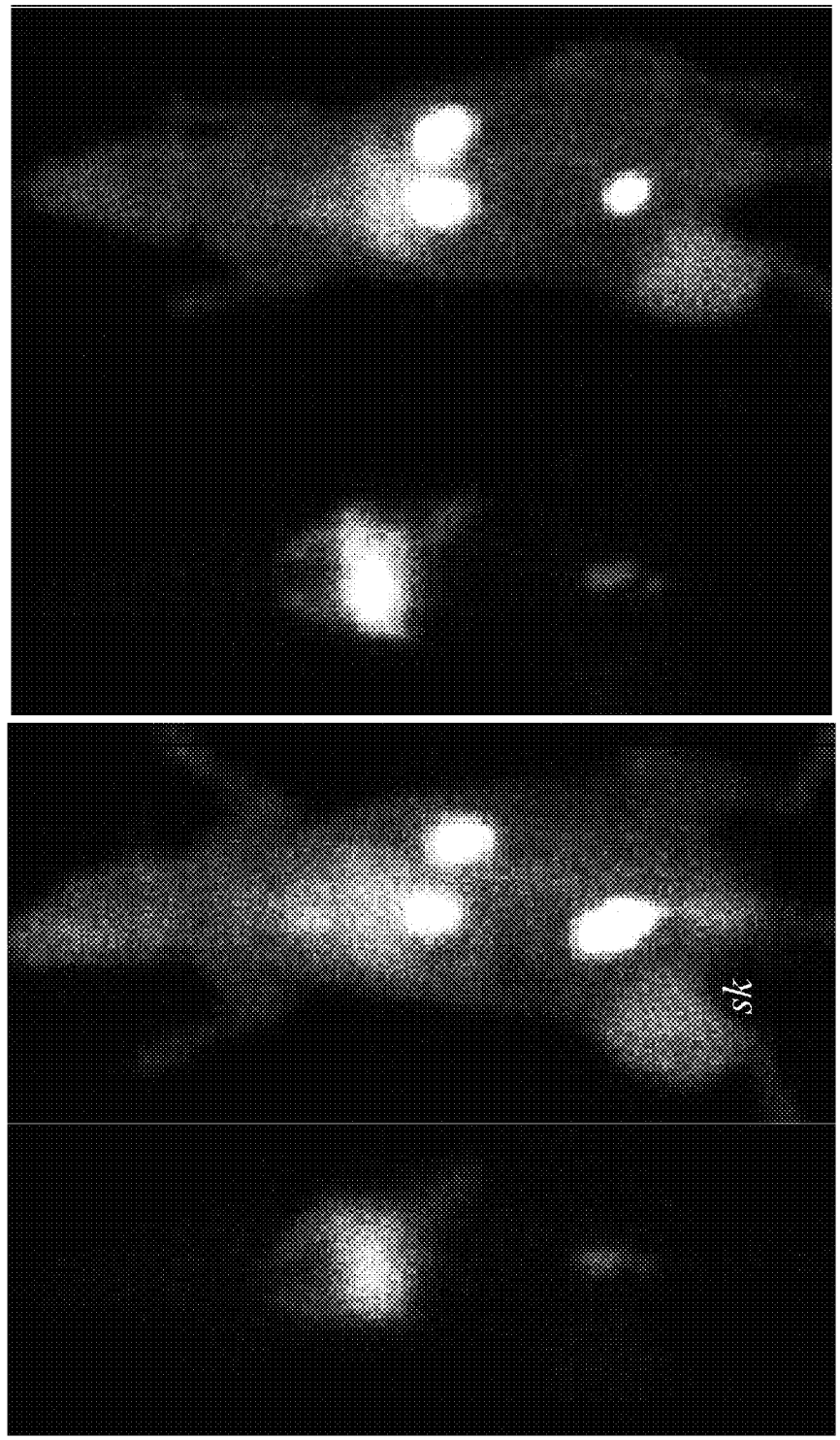
FIG. 12 the image of mice (with breast cancer cells on the legs) on γ-camera after the nuclide contrast medium is intravenous injected.

The final products (FIGS. 9, 10, 11) have yield of (62%). The purification method is easy. The raw product (aspartic acid-aspartic acid-methyl-nitroimidazole) has a purity of higher than 90%.

A. Synthesis of Compound 1

4.2 mL triethylamine (30.0 mmol), 2.6 g 1-(2-ethylamino)-2-methyl-5-nitroimidazole (10.0 mmol) and 1.7 mL phosphoryl cyanide (10.0 mmol) are added sequentially to 50 mL dry trifluoacetic acid containing 3.0 g 2-isobutyric acid amino-5-tertbutyl-L-glutamate (10.0 mmol) and the solution is stirred at room temperature for 3 hours. 100 mL dichloromethane is then added into the mixture. The reaction mixture is washed with water twice (50-60 mL each time) and dried with MgSO$_4$. The final products are separated using silica gel column. Dichloromethane and ethanol are in the mobile phase in a volume ratio of 4:1. 4.0 g compound 1 is obtained (product yield: 88%).

B. Synthesis of Compound 2: Troimidazole 2.3 g (5.0 mmol) the compound 1 is dissolved in 40 mL NaOH/ethanol solution (20 mL, 1.0 M NaOH and 20 mL ethanol) and the solution is stirred for 12 hours. The solution has been dried. The white solid product is separated using silica gel column. Water and ethanol are in the mobile phase in a volume ratio of 3:7. 1.8 g compound 2 is obtained (product yield: 91%).

C. Synthesis of Compound 3

0.4 g (1.0 mmol) the compound 1 is dissolved in 10 mL dry dichloromethane solution. 0.7 mL (5.0 mmol) triethylamine. 0.28 g hydrochloric acid ditertiarybutyl-L-aspartic ester (1.0 mmol) and 0.16 mL phosphoryl dicyanide are added sequentially at room temperature into the dichloromethane solution. The solution is stirred for 3 hours. 20 mL dichloromethane is then added into the mixture. The reaction mixture is washed with water twice (20-30 mL each time) and dried with $MgSO_4$. The final products are separated using silica gel column. Dichloromethane and ethanol are in the mobile phase in a volume ratio of 95:5. 0.46 g compound 3 is obtained (product yield: 74%).

D. synthesis of Compound 4: (1-(2-α-L-glutamine (β-L-asparaginyl)ethyl)-2-methyl-5-nitroimidazole At 0° C., 3.1 g (5.0 mmol) the compound 3 is dissolved in 4.0 mL trifluoacetic acid. The mixture is stirred at room temperature for 20 min. Extra trifluoacetic acid is removed and a small amount of hexane is added (twice, 5-10 mL each time) to removed a small amount of trifluoacetic acid. The reaction product is dissolved in 5 mL water. The pH value is the adjusted to 8-9 with 10% NaOH. 20 mL ethanol is then added. The filtered product is re-crystallized in 30 mL water and ethanol (1:1) solution and 1.4 g compound 4 (1-(2-α-L-glutamine (β-L-asparaginyl)ethyl)-2-methyl-5-nitroimidazole (70%) is obtained.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A hypoxia contrast medium comprising a nitroimidazole or derivative thereof having a formula of formula 10

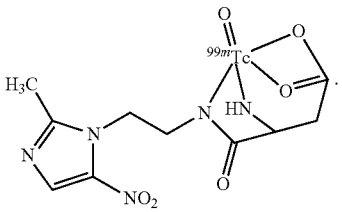

Formula 10

* * * * *